(12) United States Patent
Farrell

(10) Patent No.: US 7,214,541 B2
(45) Date of Patent: May 8, 2007

(54) VARIABLE RATE PARTICLE COUNTER AND METHOD OF USE

(75) Inventor: Gregory A. Farrell, Ridgewood, NJ (US)

(73) Assignee: Siemens Medical Solutions Diagnostics, Tarrytown, NY (US)

(*) Notice: Subject to any disclaimer, the term of this patent is extended or adjusted under 35 U.S.C. 154(b) by 631 days.

(21) Appl. No.: 09/549,036

(22) Filed: Apr. 13, 2000

(65) Prior Publication Data

US 2003/0129090 A1 Jul. 10, 2003

Related U.S. Application Data

(62) Division of application No. 09/225,937, filed on Jan. 6, 1999, now abandoned.

(51) Int. Cl.
*G01N 21/00* (2006.01)
(52) U.S. Cl. .................. 436/164; 436/10; 436/172; 422/73; 422/82.05; 422/82.07; 422/82.09; 356/335; 356/336; 356/337; 356/338
(58) Field of Classification Search .............. 422/68.1, 422/73, 82.05, 82.07, 82.09, 99; 436/10, 436/43, 164, 172, 174; 356/246, 335, 336, 356/337, 338, 339, 340, 341, 342, 72, 73
See application file for complete search history.

(56) References Cited

U.S. PATENT DOCUMENTS 3,907,437 A * 9/1975 Hirschfeld .................. 356/156
5,106,187 A * 4/1992 Bezason ....................... 356/73
5,134,445 A * 7/1992 Toge .......................... 356/336
5,470,534 A * 11/1995 Imai et al. ..................... 422/67
5,488,469 A * 1/1996 Yamamoto et al. ........... 356/72
5,517,870 A * 5/1996 Kurimura et al. ........... 356/156
5,679,575 A * 10/1997 Kubota et al. ................ 436/49
5,895,764 A * 4/1999 Sklar et al. .................... 436/63
6,184,978 B1 * 2/2001 Kasdan et al. .............. 356/246
6,317,511 B1 * 11/2001 Horiuchi ..................... 382/133
6,400,453 B1 * 6/2002 Hansen ..................... 356/237.1

* cited by examiner

*Primary Examiner*—Jill Warden
*Assistant Examiner*—Dwayne K. Handy
(74) *Attorney, Agent, or Firm*—Charles B. Rodman; Kevin Stein

(57) ABSTRACT

A variable rate particle counter for adjusting the volumetric delivery rate of fluid to a flow cell based upon an initial particle count rate in order to effectively "tune" the final dilution of sample sheath flow to the particle concentration of the sample. A sheath fluid syringe pump and a test sample syringe pump are driven by motors which are adjusted by a data analyzer. The data analyzer compares a particle count rate measured by a detection assembly to a predetermined reference value and determines if the count rate is too high or to low. Accordingly, one of several pump profiles is initiated to adjust the flow rate of the sheath fluid or test sample or both. Advantageously, the low cell count precision is improved and the upper limit cell count is expanded.

6 Claims, 3 Drawing Sheets

VARIABLE RATE PARTICLE COUNTER AND METHOD OF USE

RELATED APPLICATIONS

This application is a divisional application of U.S. Ser. No. 09/225,937, filed Jan. 6 1999 now abandoned.

This application is related to U.S. application Ser. No. 08/688,517, which issued as U.S. Pat. No. 5,788,927 on Aug. 4, 1998 for "Unified Fluid Circuit Assembly For A Clinical Hematology Instrument", which patent is commonly owned by the assignee of the present application, Bayer Corporation, and which is incorporated herein by reference in its entirety.

FIELD OF THE INVENTION

The present invention relates to instruments for performing clinical analyses of samples, more particularly to improving the counting precision of such instruments by varying the delivery rate of the samples.

BACKGROUND OF INVENTION

Analytical instruments are well known and have been commercially available for many years, in different constructions, for performing a variety of test analyses by various methods.

These instruments, such as clinical hematology lab instruments, typically receive one or a series of test samples, divide each sample into aliquots, and perform one or more tests by combining each aliquot with one or more reagents in a reaction mixture. The reaction mixtures are then analyzed in a known manner. For example, a calorimetric or similar measurement may be made on one reaction mixture while one or more other reaction mixtures may be sent to a particle counting device for a cell count.

One of the disadvantages of such known devices is that they operate with a very limited dynamic range. At low counts, precision suffers and at high counts coincident events (for example, where several cells passing at the same time through the device are counted as one cell or event) limit the range. A variety of methods are implemented in known devices to compensate for these disadvantages.

Known systems typically deliver a fixed volume of a diluted sample solution at a fixed rate for quantitative (i.e., counting) and qualitative (i.e., characterizing) the cells by optical detection means, or magnetic detection means. Techniques involving multiple counts where repetitive delivery of a predetermined volume of diluted sample is performed are sometimes employed to improve low-end precision, but this is done at the expense of sampling throughput.

Conversely, technicians dilute the test samples when cell counts are high, and consequently, the precision for very low cell counts suffers. Moreover, in many cases, the maximum cell capacity is too low for very high cell counts.

SUMMARY OF THE INVENTION

Disadvantages and limitations of the prior art are overcome by the apparatus and method of the present invention, which provide for adjusting a flow cell pump delivery rate based upon an initial count rate, to tune effectively the dilution of the sample to be examined to the cellular concentration of the sample.

It is, therefore, among the objects of the present invention to provide a method and apparatus capable of improving the precision of analyses of test samples possessing low cell counts, and having an extended upper range for very high cell counts, by varying the delivery rate of the test sample and sheath fluid.

These and other objects of the method and apparatus of the present invention are achieved in one embodiment by providing a variable rate volume particle counter comprising a sample pump for delivering a sample at a sample volumetric delivery rate and a sheath pump for delivering a sheath fluid at a sheath volumetric delivery rate into a sheath stream flow cell which suspends the sample in the sheath fluid in a laminar flow suspension which is scrutinized by a detection assembly. A data analyzer analyzes the detected information and determines control parameters necessary to achieve a predetermined sample characteristic, such as particle or cell count rate. A sample controller is coupled to the data analyzer and the sample pump for controlling the sample pump to vary the sample volumetric delivery rate in response to the control parameters, and similarly, a sheath controller is coupled to the data analyzer and the sheath pump to control the sheath pump to vary the sheath volumetric delivery rate in response to the control parameters. The delivery rate is then "tuned" to the given cell concentration of the test sample

BRIEF DESCRIPTION OF THE DRAWINGS

Further features, advantages and characteristics of the present invention will be apparent to a person of ordinary skill in the art from the following detailed discussion of a preferred embodiment, made with reference to the accompanying drawings, in which.

DETAILED DESCRIPTION OF THE DRAWINGS

Figure 1:
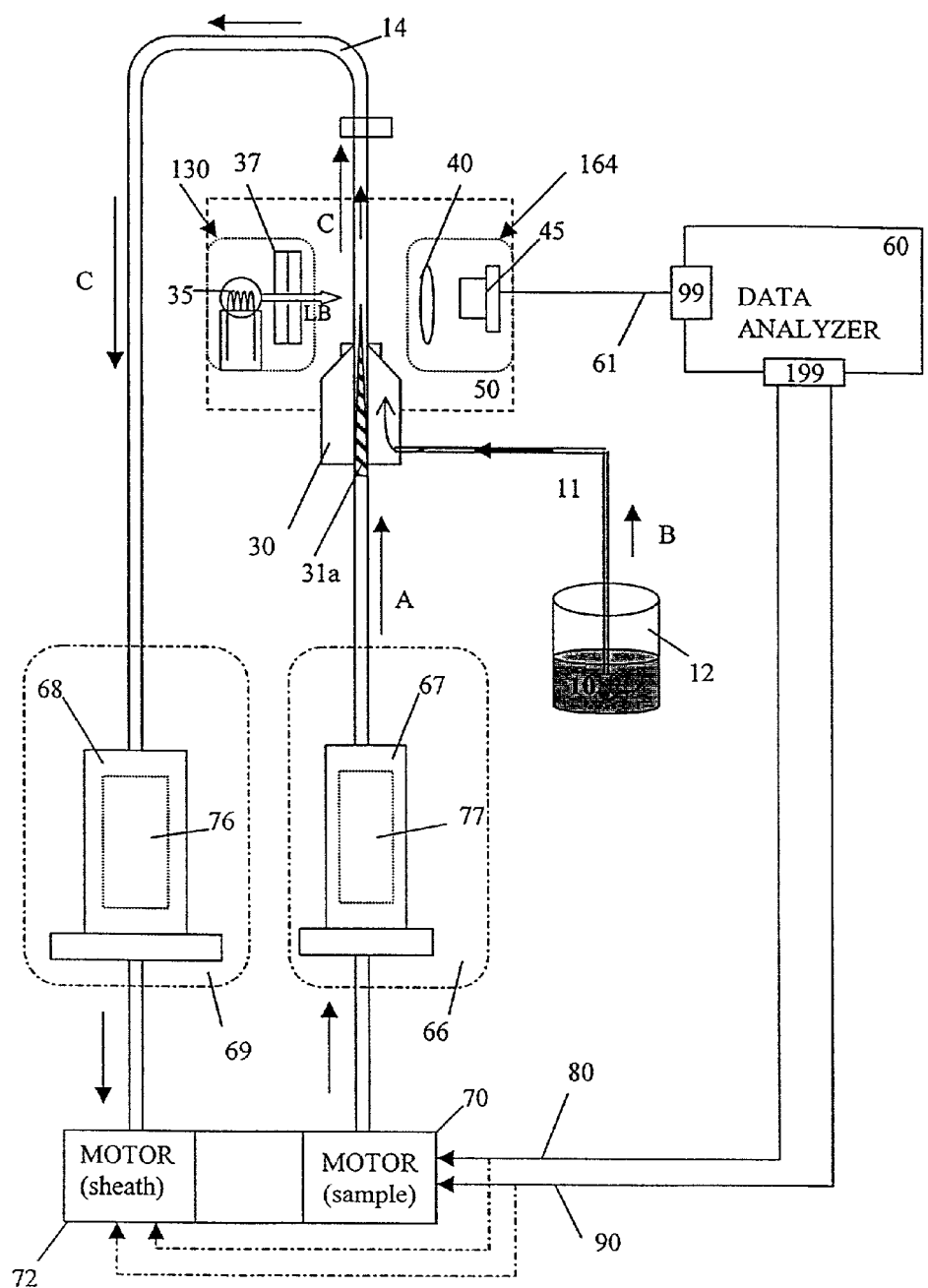
FIG. 1 is an illustrative embodiment of the variable rate volumetric particle counter of the present invention.

Referring to FIG. 1, a variable rate volumetric particle counter ("VRVPC"), in accordance with a preferred embodiment of the present invention, is shown. The VRVPC includes a sheath flow cell 30 which provides a thin stream of particles in suspension for analysis by a detection assembly. It should be recognized that the stream of particles is any fluid concentration of particles, preferably cells such as blood cells.

Sheath flow cell 30 allows presentation of cells or particles, prepared in a reaction mixture as is known, essentially one cell at a time positioned for access by detection assembly 50. The reaction mixture is drawn through a nozzle 31a into the center of a laminar flow stream 33 of a sheath liquid 10 forming a suspension of the mixture in the sheath fluid stream (a "cell suspension"). The flow velocity of the sheath liquid $\dot{Q}_{SH}$ is controlled to be much greater than the velocity of $\dot{Q}_S$ of the introduced sample reaction mixture causing the cross sectional area of the drawn suspension stream to narrow by known principles as it accelerates to the velocity of the sheath liquid. The cross section of the cell suspension stream is further narrowed by passing the sheath liquid containing the drawn cell suspension through a gradually reduced cross sectional area, again by known principles. At the point of access by detection assembly 50 (see reference numeral 119, FIG. 2) the diameter of the drawn suspension stream has been sufficiently constrained to be on the order of the diameter of one cell so that two cells cannot readily travel side-by-side in the stream. For an example description of the sheath flow cell, see U.S. Pat. No. 5,788,927 identified above.

In this illustrative embodiment, detection assembly 50 is implemented as an optical detection system which detects optical interactions with the test sample (to be discussed later) as the test sample and sheath fluid flow through the sheath flow cell 30. Optical detection system 50 comprises illuminator assembly 130 which in turn includes a light source 35 and optical filter 37, and detector assembly 164 which in turn includes lens assembly 40 and detector 45. A laser beam LB, generated by source 35, is set so as to impinge on (i.e., intersects to illuminate or interrogate) the cell suspension stream at point 119 as indicated above. Optical system 50 operates in a similar manner to the optics system, denoted element 100, in commonly owned U.S. Pat. No. 5,788,927 identified above.

Data analyzer 60 is coupled, via line 61, to one end of the optical detection system 50 and evaluates information received from the optical system 50. Data analyzer 60 determines characteristics of the test sample (e.g., cellular concentration or "count rate", which should be understood to mean the number of particles or cells in a volume of test sample per unit of time) and controls operation of motors 70, 72 in response to the resultant characteristic determination. Data analyzer 60 generally includes a microprocessor, signal processor or computer running suitable software to determine the desired characteristic (i.e., count rate) and input/output ("I/O") capabilities suitable to receive input and output commands. Data analyzer 60 in one embodiment is implementable as a PC, workstation or other microprocessor based system with appropriate I/O capabilities. Operation of the data analyzer will be discussed below.

The VRCVP includes sheath pump 69 and sample pump 66 connected through flow cell path 14. Pumps 66, 69 are respectively driven by motors 70, 72 responsive to analyzer 60, to deliver an appropriate volume of sheath fluid and sample at specific respective volumetric rates through the flow cell 30. Pumps 66, 69 are preferably syringe pumps having similar construction, including syringe pistons 76, 77 which move up and down inside cylinders 67, 68. In the preferred embodiment, the syringe piston is actuated using a lead screw actuator (not shown) connected to a belt and pulley system (not shown) which is driven by a motor 70, 72 in a conventional manner. Motors 70, 72 are preferably servo or stepper motors, which are well-known in the art. It should be noted, however, that other motors or mechanisms could alternatively be used to actuate and adjust syringe pumps 66, 69.

In the preferred embodiment, sample pump 66 will control a volumetric flow rate of the sample of $\dot{Q}_S$ in region A of flow path 14. Sheath pump 69 will control the net volumetric flow rate of $\dot{Q}_S+\dot{Q}_{SH}$ seen in region C. Sheath pump 69 will thereby control the volumetric flow rate of the sheath fluid of $\dot{Q}_{SH}$ in region B. By varying the motor speed (as will be described below), and consequently the individual pump speeds, the flow rates in regions A, B and C can be modified and controlled as desired to alter volume and dilution of the sample stream.

The ratio of sheath to sample (i.e., the dilution) is a function of the type of cell being counted. For example, in an embodiment where the present invention is implemented to count red blood cells and their density is known to be on the order of 5 million cells per cubic inch, a 1000 micro-liter per second ("μl/s") volumetric flow rate is desirable—i.e., the net flow rate $\dot{Q}_S+\dot{Q}_{SH}$ in region C is desired to be 1000 μl/s. This can be achieved by controlling sheath pump 69 to draw a volumetric flow rate of 1000 μl/s ($\dot{Q}_S+\dot{Q}_{SH}$), setting sample pump 66 to control drawing of the sample at 10 μl/s ($\dot{Q}_S$ in region A) resulting in drawing of the sheath fluid from container 12 at a volumetric flow rate of 990 μl/s ($\dot{Q}_{SH}$ in region B).

By way of another illustrative example, in an embodiment where the present invention is implemented to count white blood cells and their density is known to be on the order of 7 thousand cells per cubic inch, a 1000 μl/s volumetric flow rate is established—i.e., the net flow rate $\dot{Q}_S+\dot{Q}_{SH}$ in region C is controlled to 1000 μl/s. This can be achieved by controlling sheath pump 69 to draw a volumetric flow rate of 1000 μl/s ($\dot{Q}_S+\dot{Q}_{SH}$), setting sample pump 66 to control drawing of the sample at 50 μl/s ($\dot{Q}_S$ in region A) resulting in drawing of the sheath fluid from container 12 at a volumetric flow rate of 950 μl/s ($\dot{Q}_{SH}$ in region B).

In the preferred embodiment of the present invention, cylinders 67 and 68 each have different volumes. More preferably, cylinder 68 has a much larger volume than cylinder 67. This allows the sheath fluid 10 to be drawn into the flow cell path from a remote site, for example, a receptacle 12, connected to flow cell path 14 via line 11, as motor 72 drives sheath pump 69.

Figure 2:
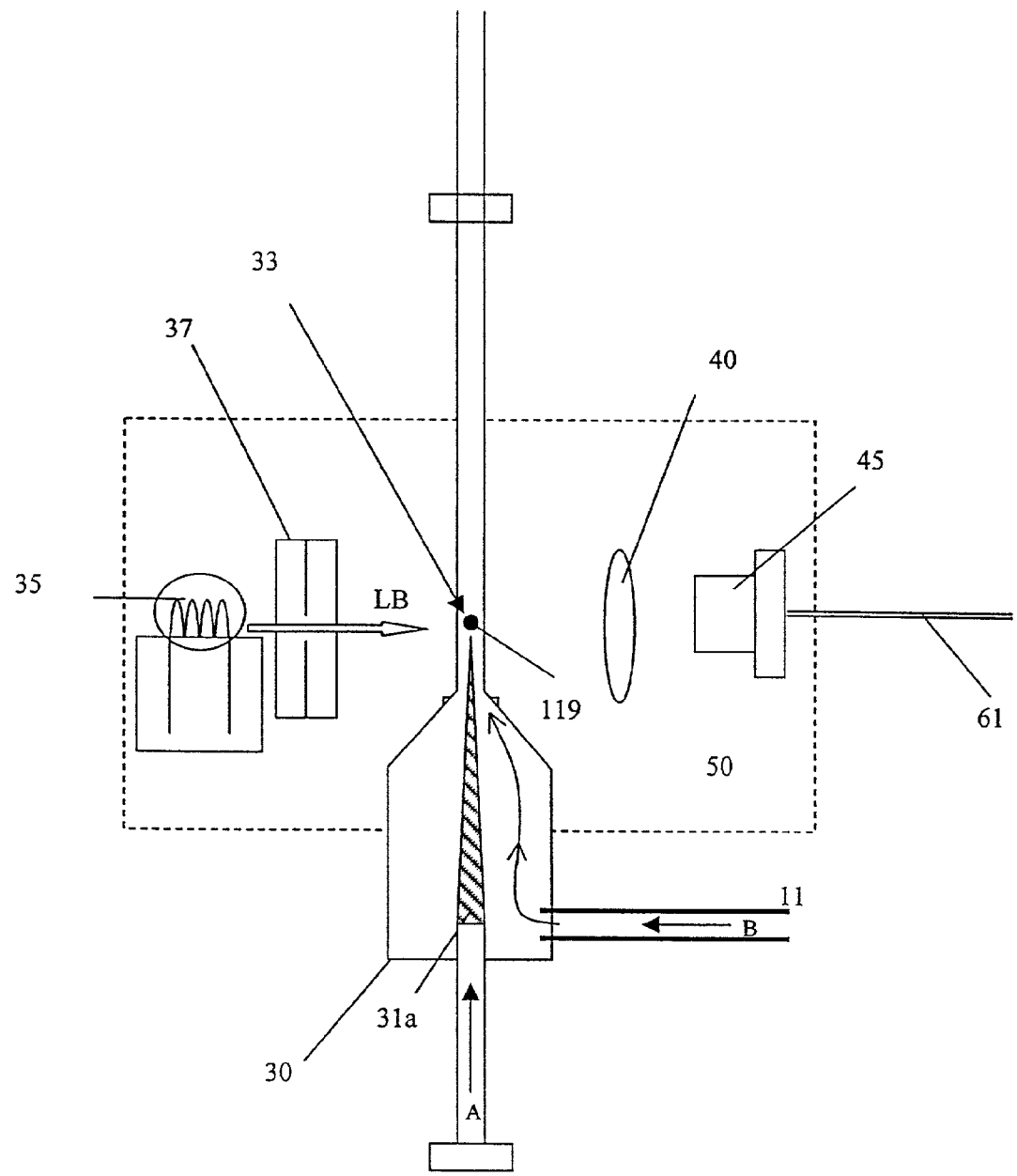
FIG. 2 is detailed illustration of the detection assembly of FIG. 1.

Referring now to FIG. 2, microprocessor-based data analyzer 60 determines characteristics of the suspended particle stream such as the particle velocity or the count of a unit volume of the test sample as it passes through the flow cell 30. Data is received via cable 61 from optical detection system 50 into an analog-to-digital ("A/D") converter 99 and stored in memory 98. Cable 61 can be, for example, a conventional transmission cable connected to an RS-232 cable port as is known. Data analyzer memory 98 contains preprogrammed (or programmable) pump profiles for processing input data to determine the desired operating state of motors 70, 72 in order to achieve an optimum pumping rate. Control motors 70, 72 are responsive to commands output through digital-to-analog converter (D/A) 199 on control lines 80, 90.

An illustrative logic sequence for data analyzer 60 to implement the method of the present invention will now be discussed.

Figure 3:
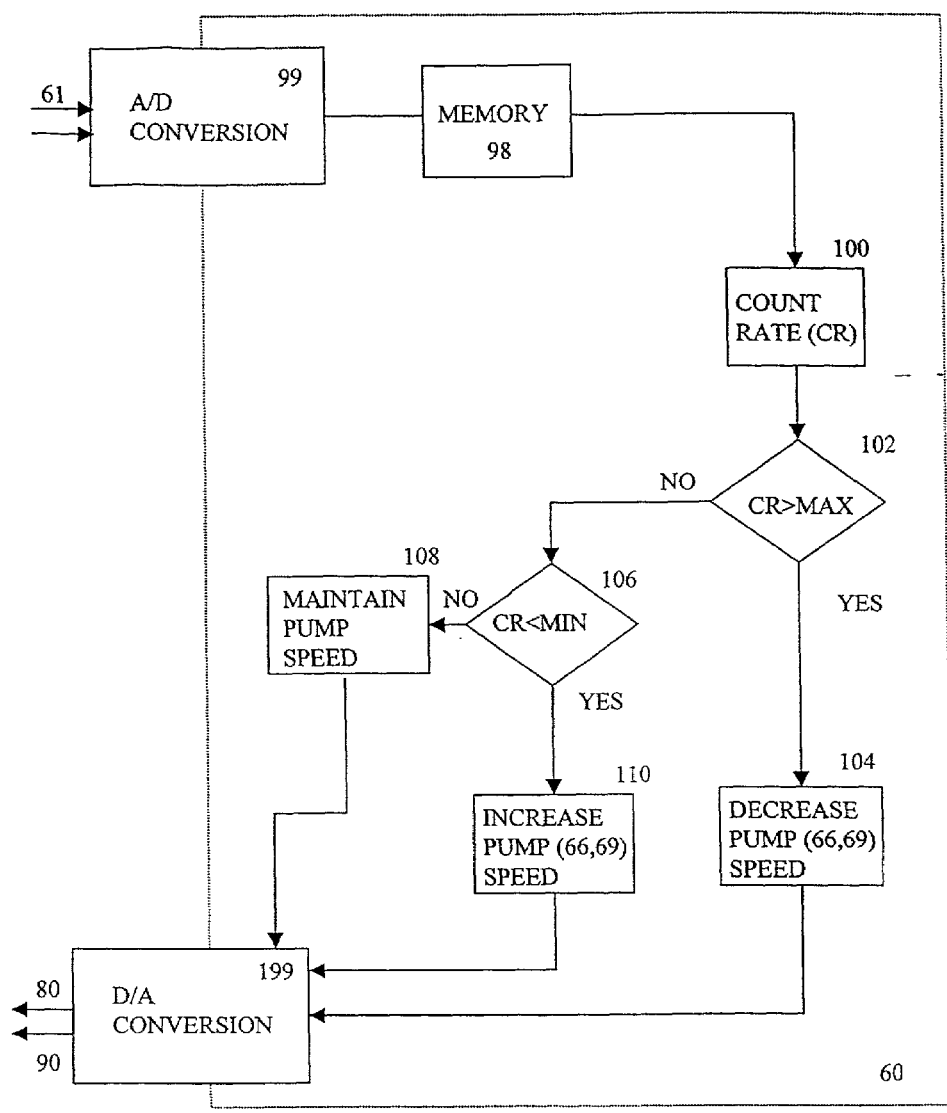
FIG. 3 is a flow diagram illustrating the logic of the data analyzer in accordance with one embodiment of the present invention.

Referring to FIG. 3, in step 100, the data analyzer determines the count rate CR representing the number of particles, e.g., blood cells, in the test sample cell suspension. At step 102, it is determined if the count rate is at a maximum. In this case, the number of cells or particles counted in step 100 is compared to a stored reference value MAX. If the count rate is at a maximum (i.e., CR>MAX), then at step 104, a "decrease motor speed" command is generated to consequently reduce volumetric delivery rate. If at step 102, the count CR is not greater than the maximum value MAX, then in step 106 it is determined if the count rate is below a predetermined minimum value MIN. If the count rate is not below the minimum value, (i.e., the output at step 66 is no), then the speed of motors 70, 72 is maintained. (Depending on the type of motor used, either no command is used to maintain motor speed or a steady state command is generated to maintain speed as will be understood by one skilled in the art.) In step 106, if the count rate is less than the minimum value MIN, an "increase motor speed" command is generated at step 110 to increase volumetric delivery rate and consequently the count rate.

Motor speed commands are then processed through D/A converter 199 for output to motors 70, 72.

In operation, pumps 66, 69 can be driven using more than one preprogrammed pump profile. Each pump profile can be downloaded from a memory 98 of analyzer 60 to determine an optimal flow rate of the sheath fluid and the test sample as each passes through the flow cell 30 for a given testing duration. In one embodiment, the optimal flow rate is determined by varying the flow rate of either the test sample or the sheath liquid. Alternatively, both flow rates could be changed simultaneously. While two to three pump profiles are typically used, it will be understood that more or less profiles may also be implemented as desired.

Primary control is effected through sample pump 66. For example, when a high count sample is being analyzed, in order to eliminate coincidence effects, $\dot{Q}_S$ is decreased. Where a low count is encountered, $\dot{Q}_S$ is increased. If the volume delivery rate of sheath pump 69 is not modified, a change in $\dot{Q}_{SH}$ will result which is inversely proportional to the change in $\dot{Q}_S$ as the net flow rate remains constant and is defined by the relation $\dot{Q}_S+\dot{Q}_{SH}$.

A factor to be considered in determining flow rate control is that the stream flow at point 119, i.e., the net volumetric rate of $\dot{Q}_S+\dot{Q}_{SH}$, is limited by the capabilities of the optical detection system. Where $\dot{Q}_S$ is increased as discussed above, the diameter to the cell stream at point 119 may increase as well resulting in possible coincident count difficulties, for which the net flow rate may also be commanded to increase to keep the analysis stream within the limits of the optical system.

Alternatively, the pump profiles may be downloaded in pump profile segments corresponding to different steps in the logic flow for the data analyzer 60. For example, in one embodiment, one segment introduces the particle suspension at a predetermined rate, and step 100' is executed to determine the particle count. In response, a second segment is initiated wherein steps 102' and 106' are performed. Another pump profile is then selected to execute steps 104', 108' and 110. It is to be understood that more than one reference value may be used in steps 102' or 106' to adjust the flow rate to a desired flow level and one or more of steps 104', 108' and 110' followed by steps 100' and one or more of steps 102' or 106' could be repeated in sequence to obtain a desired rate.

If the pump profile and flow rate are set for normal or low cellular concentration, pumps 66, 69 would be slowed down for a higher count. If the sheath flow profile and flow rate are not altered, the velocity of the cells traversing the flow cell will remain constant although the count rate and particle stream cross-sectional diameter will decrease. The total volume counted can be decreased proportionately to maintain precision within count time constraints.

Alternatively, sheath fluid flow may be adjusted to maintain stream diameter while altering the cell velocity. The volume counted may also be a function of the linear travel of pumps 66, 69 which can be determined, for example, by counting the number of revolutions of lead screw actuator or via utilization of a linear potentiometer.

Advantageously, "tuning" the particle rate to an optimum value improves the low count precision and extends the upper limit of the count rate by using a variable rate pump as described herein. Consequently, the dynamic range, the volume of fluid passing through flow cell 30 per unit time is expanded.

The present invention has been described with reference to specific embodiments thereof. It will be understood by one skilled in the art that these are not exclusive embodiments, and while the foregoing description of illustrative embodiments provides many specificities, these enabling details should not be construed as limiting the scope of the invention. It will be readily understood by those persons skilled in the art that the present invention is susceptible to many modifications, adaptations, and equivalent implementations without departing from the scope of this invention and without diminishing its advantages

I claim:

1. A method for improving the precision in counting the number of particles or cells suspended in a given volume of a test sample wherein the number of particles or cells ranges from low particle/cell counts to high particle/cell counts, comprising:
    a) delivering a sheath stream of the test sample at a first volumetric flow rate to a particle counting means to count the number of particles or cells in the test sample, wherein the sheath stream has a cross-sectional diameter adapted to deliver to said particle counting means substantially one particle or cell of the test sample at a time;
    b) making an initial count at the first volumetric flow rate of the particles or cells of said test sample per unit time with said particle counting means;
    c) comparing the initial count of the number of cells or particles in the test sample to a reference value;
    d) adjusting the flow rate of the test sample to a second volumetric flow rate based on the comparative number of cells or particles in the test sample to the reference value, thereby improving the precision of the particle counting means in counting the number of cells or particles in the test sample.

2. The method of claim 1, wherein the second volumetric flow rate optimizes the ability of the detection means to make a precise count of the particles or cells in the test sample.

3. The method of claim 1, wherein the test sample is a hematology sample.

4. The method of claim 1, wherein the first volumetric flow rate of the sheath fluid is at laminar flow.

5. The method of claim 1, wherein the detection means is optical.

6. The method of claim 1, wherein the detection means is a laser beam.

* * * * *